United States Patent [19]

Watson et al.

[11] 4,188,793

[45] Feb. 19, 1980

[54] CONDENSATION OF VAPOR OF ORGANIC LIQUIDS

[75] Inventors: Richard W. Watson, Derby; William J. Grant, London; David J. Graham, Loughborough, all of England

[73] Assignee: BOC Limited, England

[21] Appl. No.: 818,807

[22] Filed: Jul. 25, 1977

[30] Foreign Application Priority Data

Jul. 28, 1976 [GB] United Kingdom ............... 31525/76

[51] Int. Cl.² .......................... F17C 7/02; F17C 13/00; F25D 15/00
[52] U.S. Cl. .......................................... 62/51; 62/54; 62/119
[58] Field of Search ........................ 62/11, 54, 119, 51

[56] References Cited

U.S. PATENT DOCUMENTS

| | | | |
|---|---|---|---|
| 1,584,376 | 5/1926 | Jewell | 62/11 |
| 2,059,942 | 11/1936 | Gibson | 62/54 |
| 2,682,154 | 6/1954 | Wilkinson | 62/54 |
| 2,784,560 | 3/1957 | Johnson, Jr. | 62/54 |
| 2,944,405 | 7/1960 | Basore et al. | 62/54 |
| 3,046,750 | 7/1962 | Becker | 62/11 |
| 3,303,660 | 2/1967 | Berg | 62/51 |
| 3,780,534 | 12/1973 | Lofredo et al. | 62/11 |
| 3,798,918 | 3/1974 | Maher et al. | 62/54 |
| 3,967,938 | 7/1976 | Daeschler et al. | 62/54 |
| 4,133,663 | 1/1979 | Skinner | 62/18 |

*Primary Examiner*—Lloyd L. King
*Attorney, Agent, or Firm*—Dennison, Dennison, Meserole and Pollack

[57] ABSTRACT

In a process for condensing the vapor of a volatile liquid, such as vinyl chloride monomer, a gaseous mixture comprising the vapor of the volatile liquid and a non-flammable gas, such as nitrogen, is heat exchanged with a liquid refrigerant or vapor evolved therefrom, or both, the heat exchange being performed such that condensate of the vapor of the volatile liquid is produced at a directly or indirectly controlled temperature which is between the boiling point of the volatile liquid at atmospheric pressure and the boiling point of the refrigerant at atmospheric pressure and which is also between the boiling and freezing points of the volatile liquid at the prevailing pressure at which the condensate is formed, the non-flammable gas remaining uncondensed; the condensate is collected; the uncondensed gas is warmed to a temperature, and then vented to the atmosphere.

19 Claims, 6 Drawing Figures

CONDENSATION OF VAPOR OF ORGANIC LIQUIDS

This invention relates to a process and apparatus for liquefying, or condensing, volatile vapours.

In many processes for the manufacture of chemicals an effluent gas containing a significant proportion of a toxic or otherwise undesirable vapour is often produced. Moreover, such toxic or otherwise undesirable vapours may be vented from plants for handling such chemicals. Such loss of vapour is wasteful and may constitute a health hazard.

In recent years, much technological activity has been devoted to finding new methods of dealing with toxic gaseous effluents. One notable problem arises in plants which produce vinyl chloride in monomeric form or which use the monomer as a feedstock to manufacture other chemicals (for example, polyvinyl chloride). Since vinyl chloride is exceedingly toxic it is generally considered unsafe to allow the concentration of vinyl chloride in any exhaust gas to exceed more than 10 parts per million (ppm). Indeed, some authorities (notably in the USA) stipulate that the concentration of vinyl chloride should not exceed two ppm.

It has been proposed to remove vinyl chloride from exhaust gases by passing the exhaust gases through an incinerator by which means the vinyl chloride is converted into less toxic compounds or by passing the exhaust gases through an adsorption bed of activated carbon whereby the vinyl chloride is adsorbed. In practical use, however, it has been found that these methods have certain drawbacks.

According to the present invention there is provided a process for condensing the vapour of a volatile liquid, in which a gaseous mixture comprising the vapour of the volatile liquid and a non-flammable gas is heat exchanged directly or indirectly with a liquid refrigerant (as hereinafter defined) or vapour evolved therefrom, or both, the heat exchanged being performed such that condensate of the vapour of the volatile liquid is produced at a directly or indirectly controlled temperature which is between the boiling point of the volatile liquid at atmospheric pressure and the boiling point of the refrigerant at atmospheric pressure, and which is also between the boiling and freezing points of the volatile liquid at the prevailing pressure at which the condensate is formed, the non-flammable gas remaining uncondensed; the condensate is collected; the uncondensed gas is warmed to a temperature at or neat to ambient temperature, then vented to the atmosphere.

It is to be appreciated that the substance to be condensed need not be a liquid at ambient temperature and atmospheric pressure. For example, vinyl chloride has a boiling point at atmospheric pressure of about $-14°$ C. Indeed, the invention is particularly suitable for condensing the vapours of substances whose boiling points at atmospheric pressure are below ambient temperature.

It is an object of the invention to provide a readily controlled process for condensing the vapour of a volatile liquid such as vinyl chloride.

According to the present invention there is provided a process for condensing the vapour of a volatile liquid, in which a gaseous mixture comprising the vapour of the volatile liquid and a non-flammable gas is heat exchanged directly or indirectly with a liquid refrigerant (as hereinafter defined) or vapour evolved therefrom, or both, the heat exchanged being performed such that condensate of the vapour of the volatile liquid is produced at a directly or indirectly controlled temperature which is between the boiling point of the volatile liquid at atmospheric pressure and the boiling point of the refrigerant at atmospheric pressure, and which is also between the boiling and freezing points of the volatile liquid at the prevailing pressure at which the condensate is formed, the non-flammable gas remaining uncondensed; the condensate is collected; the uncondensed gas is warmed to a temperature at or near to ambient temperature, then vented to the atmosphere.

It is to be appreciated that the substance to be condensed need not be a liquid at ambient temperature and atmospheric pressure. For example, vinyl chloride has a boiling point at atmospheric pressure of about $-14°$ C. Indeed, the invention is particularly suitable for condensing the vapours of substances whose boiling points at atmospheric pressure are below ambient temperature. Nonetheless, the invention is also useful for condensing the vapours of compounds which although liquid at ambient temperature and atmospheric pressure have a substantial vapour pressure at such pressure and temperature. For example, the invention may be used to condense petroleum vapour. Examples of other vapours that may be condensed by the process and apparatus according to the present invention are vinyl acetate, ethylene dichloride and acrylonitrile. The invention is not, however, limited to the examples mentioned in this paragraph.

By the term liquid refrigerant, as used herein, is meant a liquid which at atmospheric pressure has a boiling point of $-50°$ C. or less. The preferred liquid refrigerant is liquid nitrogen, although such cryogenic liquids as liquid methane and liquid argon may be used instead. Preferably, a single refrigerant is used.

Often the source of the vapour will be a mixture of the vapour with a non-flammable gas such as nitrogen, which gas remains in the gaseous phase at the temperature at which the vapour is to be condensed. If however, the source of the vapour to be condensed is pure, the vapour should be mixed with a non-flammable gas which does not condense with the vapour. Such a gas is nitrogen. This is preferably done even if the source of vapour is one which is a mixture of the vapour with a non-flammable gas which does not condense with the vapour. Preferably, the nitrogen or other gas is mixed with the vapour at a predetermined rate. Should such nitrogen or other gas be added to the vapour or already be mixed therewith at its source the condenser should have an outlet for the uncondensed gas.

Having a facility to add nitrogen to the incoming vapour offers a number of advantages. It makes possible purging of the condenser and the heat exchanger when the flow of incoming vapour is imtermittent. It also facilitates sensing of the temperature at which the condensate leaves the condenser if such temperature sensing is used to control the heat exchanger. Moreover, if the whole or the major portion of the incoming vapour is condensible the addition of nitrogen thereto will prevent an excessively large suction being set up on the condensation of the vapour. such suction may draw air or water into the condenser or equipment associated therewith. Such water, or carbon dioxide and water vapour in such air, would be likely to freeze, and thereby block passages through which condensed liquid is required to flow. In addition, any air drawn into the condenser could give rise to an explosive mixture therein.

If it is desired that the refrigerant should be recovered uncontaminated with the vapour to be condensed the refrigerant should be kept separate from the vapour to be condensed by choosing that the heat exchange be indirect. On the other hand, if it is not desired to recover the refrigerant or if some contamination thereof can be tolerated, the refrigerant may be directly contacted with the vapour to be condensed in order to effect the condensation (i.e. direct heat exchange) Direct heat exchange offer the advantage that it makes possible a plant more simple than that required if the refrigerant and the vapour to be condensed are kept separate. However, when condensing highly toxic substances such as vinyl chloride it will usually be desirable to ensure that the refrigerant remains uncontaminated by the toxic substance.

Desirably the condenser includes at least one conduit, typically a pipe or tube, if desired, helically coiled, through which one of the vapour to be condensed and any gas mixed therewith, or the refrigerant is passed, the other being contacted with the external surface of the or each conduit. The, or each, pipe or tube is preferably or metal having good heat conductive properties and being suitable for use at temperatures below ambient, for example copper.

Several different embodiments of condenser may be employed in the method according to the present invention.

The condenser may for example include a container through which the or each conduit passes, which container is adapted to receive liquid refrigerant such that in operation the, or each, conduit is at least partially immersed in the liquid refrigerant whereby the temperature of the vapour, and the gas mixed therewith, passing therethrough, is reduced to the temperature at which the cryogenic liquid boils. This temperature may be chosen by subjecting the liquid refrigerant in the container to the selected pressure. The greater the pressure to which the liquid refrigerant is subjected the higher will be its boiling point. The pressure to which the liquid refrigerant is subjected may be that used to transfer the liquid refrigerant into the container. For example, if the container of liquid refrigerant is a so-called "vacuum-insulated evaporator" (VIE) the transfer pressure may be effected by creating a chosen pressure in the ullage space of the evaporator. If this pressure is not sufficient a pump may be used to create an even greater transfer pressure.

In an alternative form of condenser the outside of the, or each, heat exchange conduit tube, (eg; pipe or coil) may be contacted by a stream of streams of liquid refrigerant or the vapour thereof, or both, rather than by a stationary body of liquid refrigerant. For example, the liquid refrigerant may be sprayed onto the, or each, heat exchange conduit. For this purpose, a number of spray nozzles may be disposed circumferentially about the, or each, heat exchange tube or pipe. Control of the heat exchange may be effected by monitoring either the temperature of the liquid condensate or the outgoing uncondensed gas. Preferably, the latter temperature is sensed. The sensed temperature may be used to control the heat exchange automatically. For example, a stop valve in the pipe supplying the liquid refrigerant to be heat exchanged may be arranged to be open only when the sensed temperature is above a chosen value. Thus, liquid refrigerant is sprayed only when the sensed temperature is above the chosen value. The stop valve may for example be a pneumatically or electrically operated valve. The advantage of such a condenser is that it enables the cryogenic liquid to be used economically and is readily able to achieve temperatures well above the boiling point (at atmospheric pressure) of the liquid refrigerant.

In alternative forms of condenser the, or each, heat exchange coil, tube or pipe is contacted with gas evaporated from the liquid refrigerant. In one such form of the condenser liquid refrigerant is adapted to be received in the same vessel as that in which the, or each, heat exchange pipe tube or coil is received. Typically, the lower end of the or each heat exchange coil, pipe or tube is situated in a vessel well above the base thereof, the space therebelow being adapted to hold liquid refrigerant and having a heater associated therewith for evaporating the liquid refrigerant. The heater is preferably a coil or tube through which warm heat exchange fluid can be passed. The warm heat exchange fluid may be nitrogen at or near ambient temperature. By choosing the rate at which the warm heat exchange fluid is passed through the heater the rate at which the cryogenic liquid is evaporated and hence the temperature of the condensate may be controlled. Typically, the temperature of the condensate leaving the condenser is sensed by a temperature sensor (or alternatively the temperature of the uncondensed gas if any) leaving the condenser is sensed and the sensed temperature is used to control, preferably automatically the setting of the flow-control valve in the inlet to the heater so as to keep the sensed temperature at or close to a chosen value.

An alternative form of heater that can be used is an electrical heater. In this example the sensed temperature may be used to actuate the electrical heater only if it is above a chosen temperature.

In preferred alternatives to the form of condenser in which a stationary volume of liquid refrigerant is evaporated in situ in the condenser itself, liquid refrigerant is evaporated outside the condenser. In one such alternative a stream or spray of liquid refrigerant is combined with evaporated refrigerant leaving the condenser after heat exchange with the vapour to be condensed and then passed into the condenser. A blower may be used in order to recirculate the evaporated refrigerant. The blower may be downstream of where the liquid refrigerant joins the vapour being recirculated but is preferably upstream thereof. The temperature of the refrigerant entering the condenser (and hence the temperature of the condensate) is preferably kept at or near to a chosen temperature by controlling the introduction of liquid refrigerant into the vapour being recirculated. This may be done by sensing the temperature of the vapour at or near to its inlet to the condenser and adjusting the setting of a valve in a pipe from which the liquid refrigerant vapour. The adjustment may be effected automatically by arranging for the temperature sensor to generate signals which actuate a pneumatically, electrically or pneumatically/electrically operated valve.

Another way of evaporating liquid refrigerant is to heat exchange the liquid refrigerant with a fluid which is preferably above ambient temperature which is kept separate from the refrigerant, and which is not heat exchanged with the gaseous mixture to be condensed. A preferred heat exchange fluid is steam. The evaporated refrigerant may be supplied to the condenser at or close to a chosen temperature by controlling the amount of fluid that is heat exchanged with the liquid refrigerant. This may be achieved by sensing the temperature of the gas leaving the heater and feeding appropriate signals to a flow-control valve which controls the inlet of the heat exchange fluid to the heat exchanger in which the liquid refrigerant is evaporated so as to keep the sensed temperature at or near to the chosen temperature. The valve may be electrically operated, pneumatically operated or electrically and pneumatically operated. The temperature of the condensate may be controlled by controlling the rate at which the evaporated refrigerant is passed through the condenser. This is preferably achieved by positioning a temperature sensor in the condenser such that it is contacted by the condensate or any uncondensed gas (typically nitrogen) and arranging for the temperature sensor to feed signals to a valve controlling the rate of entry of evaporated refrigerant into the condenser. The valve may be electrically and/or pneumatically operated.

A suitable form of condenser for effecting heat exchange between the vapour to be condensed and evaporated refrigerant is a shell-and-tube heat exchanger. If desired, the evaporated refrigerant may be passed through the tubes and the gas mixture containing vapour to be condensed passed through the space between the shell and tubes. However, it is preferred that the gas mixture containing the vapour to be condensed be passed through the tubes and the evaporated refrigerant passed through the space between the shell and tubes.

The advantage of forms of condenser, which condense the vapour by heat exchange with evaporated refrigerant only, is that a temperature well above the boiling point of the refrigerant liquid (at atmospheric pressure) may readily be achieved.

If it is desired to use a "direct contact" condenser the incoming gas mixture containing the vapour to be condensed is preferably pre-cooled by heat exchanged with the said uncondensed gas. If any condensate is formed during the pre cooling it is preferably separated from the uncondensed gas before the latter is passed into the condenser. In the condenser, refrigerant liquid (preferably liquid nitrogen) is arranged to impinge upon the vapour to be condensed. The condensate and uncondensed gas are then preferably passed into a combined demister and separator in which the uncondensed gas is disengaged from the condensate. The uncondensed gas may then be heat exchanged with the incoming gas mixture containing the vapour to be condensed so as to pre-cool the latter.

The temperature at which the condensate is collected is preferably controlled by sensing its temperature, or that of the uncondensed gas before it is heat exchanged with incoming gaseous mixture, and employing signals generated by the temperature sensor to control the setting of a flow-control valve in a conduit through which the liquid refrigerant is supplied to the condenser so as to keep the sensed temperature at or neat to a chosen value. The valve may be pneumatically and/or electrically operated.

If desired, when there is not direct contact between the liquid refrigerant and the gaseous mixture, the condensate together with uncondensed gas may flow, typically under gravity, into a phase separator adapted to disengage the gas from the liquid. The liquid condensate may pass, typically under gravity, into a product collection/transfer vessel. This vessel preferably has a valved inlet for the condensate and a separate valved inlet for inert non-flammable gas such as nitrogen. In addition, the tank preferably has a valved outlet for the transfer of the condensate and a valved outlet for venting the non-flammable gas from the container.

Preferably the valves are operated in sequence to stop the flow of condensate into the vessel, pass nitrogen into the vessel, discharge the product therefrom and vent nitrogen therefrom, the sequence being initiated when the level of condensate in the vessel reaches a chosen level.

Preferably, the evaporated refrigerant from the condenser and the uncondensed gas therefrom are passed through a heater or heat exchanger so as to warm them to atmospheric temperature, or a temperature near thereto. The evaporated refrigerant may then be used in another process. The uncondensed gas may be discharged to the stack of the plant from which the vapour to be condensed originates.

It is to be appreciated that the temperature at which the condensate is supplied to the collection vessel should be such that its vapour pressure does not exceed a level at which the concentration thereof in any uncondensed gas does not exceed a chosen level. For some compounds having a relatively low vapour pressure it may be possible to arrange for this temperature to be such that the uncondensed gas may be vented to the atmosphere without further treatment. However, for particularly volatile substances such as vinyl chloride it will generally be desirable to mix the uncondensed gas with an appropriate volume of air of other gas before discharging it to the atmosphere. Thus, if the vapour is vinyl chloride and the mixture received by the condenser consists of vinyl chloride and nitrogen, and if it be desired that the gas discharged from the plant should not have a concentration of vinyl chloride in excess of 10 ppm the nitrogen stream may be mixed with air or other gas in the stack of the plant in which the vinyl chloride is manufactured or used. For example, if the vapour pressure of the condensed vinyl chloride is equivalent to a concentration of 100 ppm the nitrogen may be mixed with 10 times its volume of air in the stack.

If the gaseous mixture contains impurities such as water and carbon dioxide which freeze at the temperature at which the condensate is produced it is preferable to remove such impurities before condensation. This is conveniently done by passing the incoming gaseous mixture through a reversing heat exchanger in heat exchange with one or both of the cold gaseous stream leaving the condenser. Typically, two reversing heat exchangers can be employed, and the fluids to be heat exchanged may be switched from one to the other at regular intervals of, say, ½ hour. The operation of reversing heat exchangers is well known from for example plants for the cryogenic separation of air. If desired, a differential pressure detector may be connected across the, or each, reversing heat exchanger to detect the amount of solids frozen on the heat exchange surface of the, or each, reversing heat exchanger.

If the vapour contains only small quantities of such impurities and if it is tolerable to purge the condenser and ancillary equipment at regular intervals with, for example, warm nitrogen the impurities may be allowed to freeze in the condenser or ancillary equipment, the frozen impurities then being removed by being sublimed or evaporated by the warm nitrogen.

One convenient form of heater or heat exchanger for warming the outgoing uncondensed gas and evaporated refrigerant streams is a bath containing hot water.

The water may be heated by steam, the supply of which is controlled by a flow-control valve sensitive to variations in temperature in the bath.

If desired, the incoming vapour and any gas mixed therewith or to be mixed therewith, may be heat exchanged with the outgoing evaporated nitrogen and any uncondensed gas before being admitted to the condenser. This makes possible a reduction in the consumption of cryogenic liquid and steam, if the latter is used to warm the outgoing gases.

By using only a single refrigerant, for example liquid nitrogen and/or its vapour, control of the process is facilitated.

The invention also includes within its scope vapour condensed by the process according to the present invention.

The process and apparatus according to the present invention will now be described with reference to the accompanying drawings of which;

Figure 1:
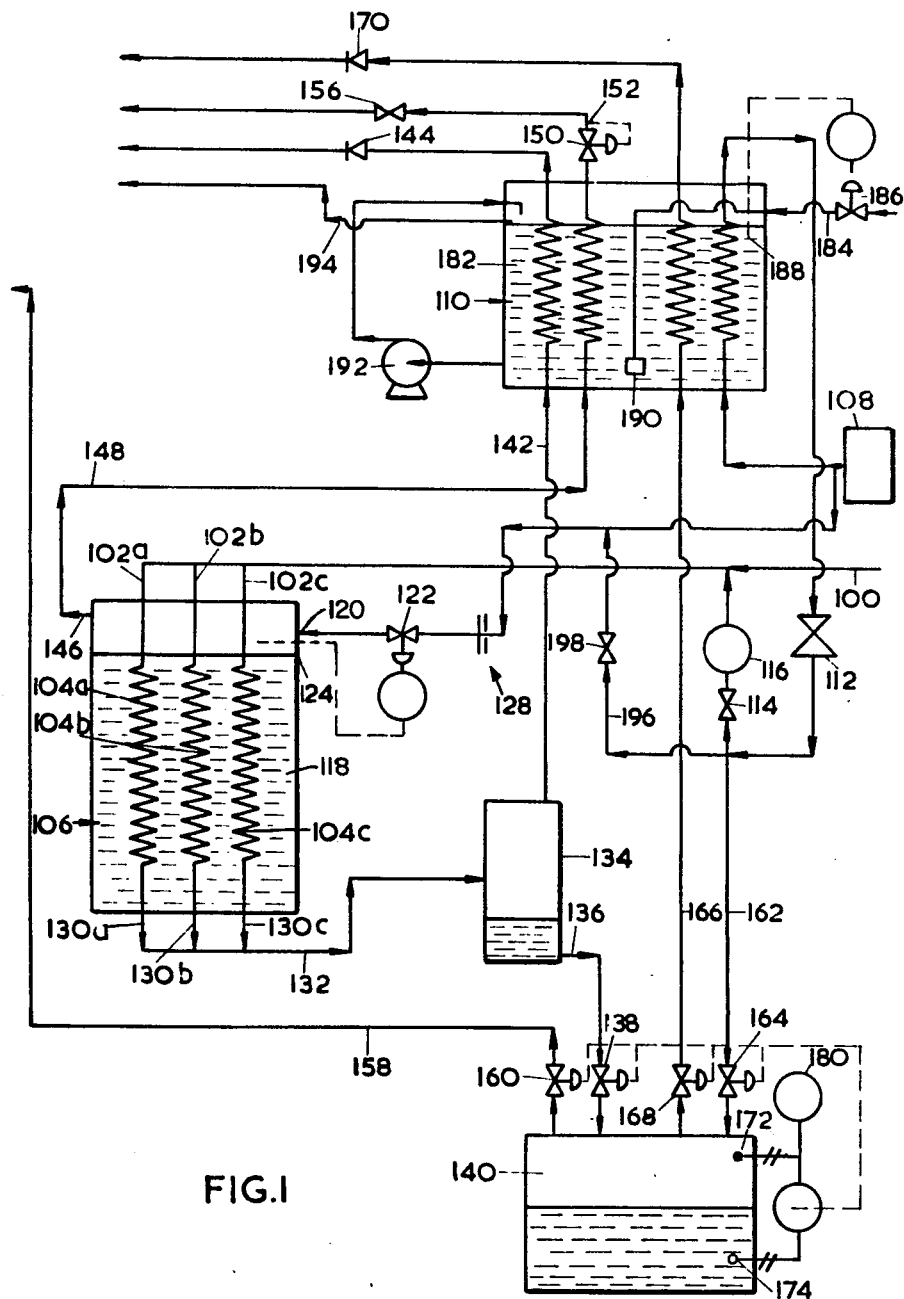
FIG. 1 is a flow diagram illustrating one plant for performing the process according to the present invention.

With reference to FIG. 1, process gas which may for example include or consist of vinyl chloride mixed with nitrogen enters the plant through pipeline 100 and passes therethrough into the inlets 102 (a), 102 (b) and 102 (c) of vertically disposed heat exchange coils 104 (a), 104 (b), and 104 (c) which extends vertically downwards therefrom and which form part of a condenser 106.

Liquid nitrogen from a vacuum insulated vessel 108 is passed through a heat exchanger 110 in which it is evaporated and warmed to approximately ambient temperature.

From the heat exchanger 110 the resulting nitrogen gas passes through an expansion valve 112 and a manual control valve 114 whereby its pressure is reduced to that of the process gas entering the pipeline 100.

The expanded nitrogen is metered through a flow indicator 116 which is controlled by the valve 114 upstream thereof and which is adapted to introduce nitrogen into the pipeline 100 at a predetermined rate.

The mixture of nitrogen and vinyl chloride as it passes through the heat exchange coils 104 is cooled by means of volume 118 of liquid nitrogen in which the coils 104 are immersed.

The liquid nitrogen is introduced into the condenser 106 from the vacuum insulated evaporator 108 under a chosen pressure created in the ullage space of the vessel 108.

Entry of the liquid nitrogen into the condenser 106 through inlet 120 is controlled by a pneumatically or electrically operated valve 122 positioned upstream of the inlet 120. The valve 122 is opened when a level sensor 124 is positioned inside the condenser 106 at a chosen level fails to detect the presence of liquid nitrogen.

By this means the level of liquid nitrogen in the condenser 106 is kept at a chosen level.

This level may be chosen such that the coils 104 are totally or partially immersed in the liquid nitrogen If desired, baffles (not shown) may be located in the ullage space of the condenser 106 to direct evaporated nitrogen over the upper portions of the heat exchange coils 106, the level sensor 124 being arranged to keep the coils only partially immersed in liquid nitrogen. By this means the evaporated nitrogen as well as the liquid nitrogen may be used to reduce the temperature of the incoming process gas.

The pressure at which the nitrogen is supplied to the condenser 106 through the inlet 120 determines the temperature at which the volume of liquid nitrogen 118 boils and hence the temperature to which the mixture of nitrogen and vinyl chloride is reduced as it passes through the heat exchange coils 104. If this temperature is chosen to be well above the normal atmospheric boiling point of the liquid nitrogen ($-196°$ C.) it may not be possible to generate the required pressure in the vacuum insulated evaporator 108. In order to boost the pressure, therefore, a pump may be provided at location 128 in order to generate the required pressure.

The mixture of gaseous nitrogen and condensed vinyl chloride leaves the heat exchange coils 104 through outlets 130 (a), 130(b) and 130(c) which communicate with a pipeline 132 for feeding the liquid-gas mixture into a phase separator 134. In the phase separator 134 the liquid is disengaged from the vapour. The liquid collects at the bottom of the separator 134 and may be passed into a thermally insulated product collection/transfer tank 140 via pipeline 136 which has located therein a pneumatically or electrically operated control valve 138. The operation of the tank 140 shall be described hereinafter.

The uncondensed nitrogen rises to the top of the phase separator 134 and passes out of it through conduit 142 which extends through the heat exchanger 110 and has located therein downstream of the heat exchanger 110, a non-return valve 144. The conduit 142 comes to an end in the stack of the plant in which the vinyl chloride is made or used. As the nitrogen passes through the heat exchanger 110 so it is warmed to ambient temperature.

The condenser 106 has an outlet 146 for nitrogen evaporating from the volume 118 of liquid nitrogen therein. The outlet 146 is situated near the top of the condenser 106 and communicates with a conduit 148 which extends through the heat exchanger 110. Situated in the conduit 148 downstream of the heat exchanger 110 is a pneumatically or electrically operated flow-control valve 150 which may be set to close should the temperature sensed at 152 downstream thereof fall below a chosen value. Downstream of the valve 150 is a back pressure valve 156 set to control the pressure on its upstream side such that it is kept above a minimum chosen to be greater than the maximum pressure at which the nitrogen is required by the process operated on its downstream side. This prevents the nitrogen from being 'demanded' from the conduit 148 by equipment into which the nitrogen is passed.

Referring now to the collection/transfer tank 140, this tank has a valved outlet line 158 through which vinyl chloride may be transferred to the plant in which it is used or formed. The line 158 has an electrically or pneumatically operated valve 160 located therein. The tank 140 also has a valved inlet pipe line 162 for gaseous nitrogen. Pipeline 162 communicates with the downstream end of the expansion valve 112 and thus receives evaporated nitrogen from the evaporator 108 via the heat exchanger 110. Alternatively, a line (not shown) may be taken directly from the ullage space of the evaporator 108 via a pressure control valve (not shown) to provide cold gas for this purpose. In the line 162 is situated a pneumatically or electrically operated control valve 164. The tank 140 also has an outlet line 166 which extends through the heat exchanger 110 and comes to an end in the stack (not shown) of a plant in which the vinyl chloride is used, formed or stored. The outlet line 166 has near its inlet a pneumatically or electrically operated flow control valve 168. In addition, the line 166 has downstream of the heat exchanger 110 a non-return valve 170. This non-return valve prevents return of gas containing vinyl chloride or oxygen from the stack.

In normal operation of the tank 140, the valves 138 and 168 will remain open to permit condensed vinyl chloride to flow into the tank 140 from the phase separator 134. The other valves will generally be closed. When the level of vinyl chloride in the tank 140 reaches that of an upper level sensor 172 located therein the valves may be actuated in the following time controlled sequence. First, the valves 138 and 168 are closed to prevent further entry of vinyl chloride into the tank or venting of vapour therefrom. Second the valve 160 is opened. Third, the valve 164 is opened so as to permit nitrogen to pass into the ullage space of the tank 140 and to create in the ullage space thereof a pressure sufficient to transfer liquid from the tank 140. During the transfer period, vinyl chloride may still be condensed. The separator 134 should desirably have a sufficiently large volume to be able to collect condensate during the transfer period without the operation of the condenser 106 being impaired. When the level of liquid tank 140 has fallen to that of a lower level detector 174 the valves 164 and 160 are closed. A chosen time afterwards the valve 168 is opened to enable the ullage space of the tank to be vented, the gas passing through the heat exchanger 110 being vented to the stack. A chosen time afterwards the valve 138 is reopened so as to permit introduction of the condensed vinyl chloride into the tank 140 to take place again. If desired, the tank may be fitted with an automatic alarm 180 such that if the level of vinyl chloride therein remains at or above that of the detector 172 for a chosen time the alarm 180 will sound.

The streams passing through the heat exchanger 110 are warmed by a volume of hot water 182 maintained therein. The water 182 is heated by steam, typically at 80 p.s.i.g, admitted into the heat exchanger 110 through a pipeline 184. The pipeline 184 has disposed therein a mechanically-operated flow control valve 186. The setting of the valve 186 may be adjusted automatically by means of signals generated by a temperature sensor 188 located in the volume of water 182 so as to keep this volume of water at a chosen temperature, say, 80° C. The pipeline 184 ends in a silencer 190 through which the steam is introduced into the volume of water 182. To ensure that the water is kept at an approximately uniform temperature at all levels in the heat exchanger 110 a pump 192 may be provided so as to transfer water from the bottom of the heat exchanger 110 to a region near the top thereof. In addition, the heat exchanger 110 is provided with an outlet 194 through which excess water may be discharged.

If desired, the plant may have means for introducing warm nitrogen into the pipeline in which the valve 122 is disposed. For this purpose, an extra line 196 may be incorporated in the plant in communication with the downstream end of the nitrogen expansion valve 112. The line 196 has a shut off valve 198 disposed therein.

Figure 2:
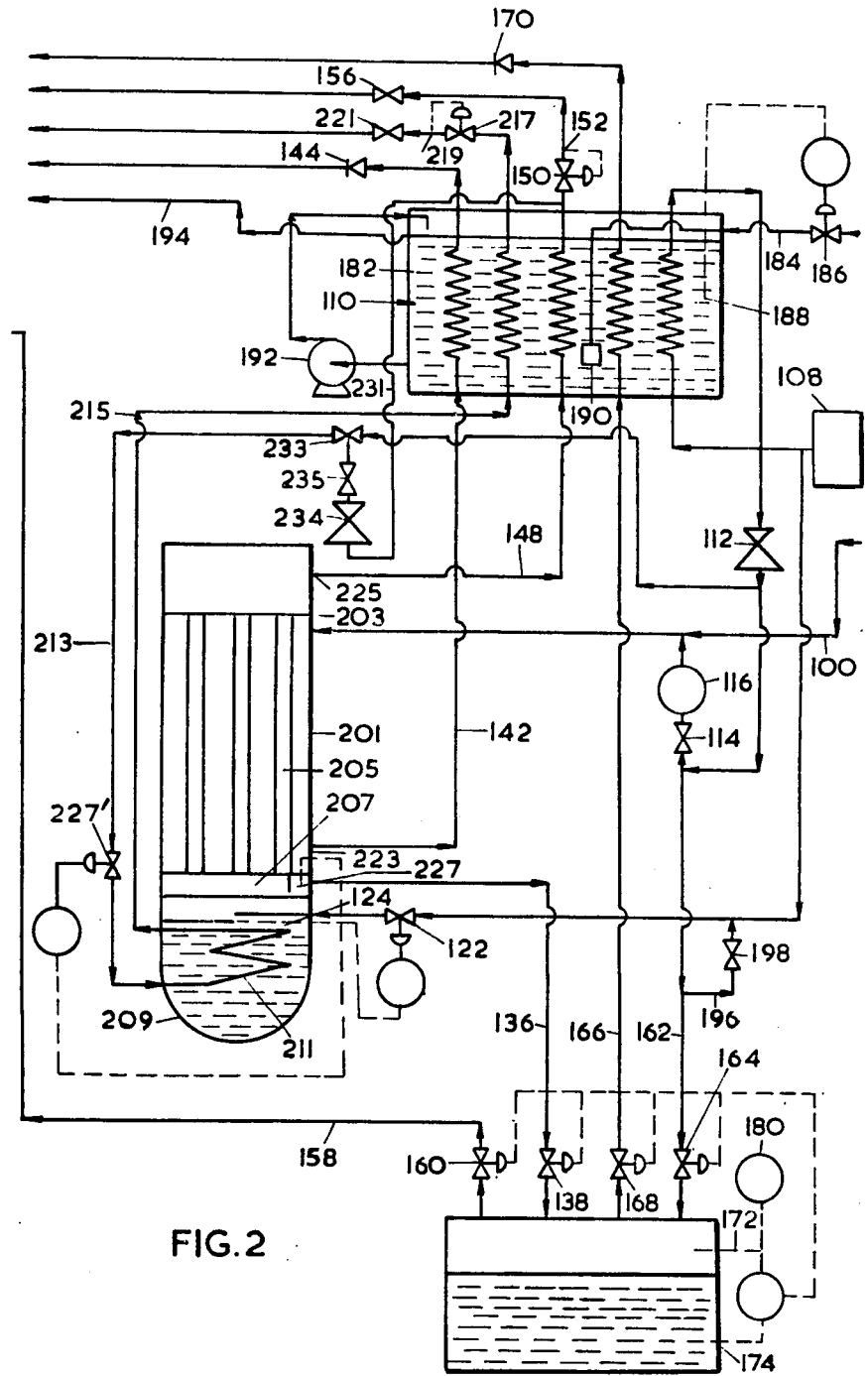
FIG. 2 is a flow diagram illustrating a second plant for performing the process according to the present invention.

Referring now to FIG. 2 of the drawings, the plant illustrated therein is generally similar to that shown in FIG. 1 but incorporates a different form of a condenser. Parts of the plant shown in FIG. 2 which have exact counter parts in the plant shown in FIG. 1 will be indicated by the same reference numerals as used in FIG. 1 and shall not be described again with reference to FIG. 2.

The process gas, consisting of nitrogen and vinyl chloride enters a condenser 201 in the form of a shell and tube heat exchanger through an inlet 203 and passes outside several vertically disposed heat exchange tubes 205. At the lower end of the condenser 201 is a collection region 207 for condensate which communicates directly with the pipe 136, though if desired a phase separator may be interposed between the two.

At the bottom of the condenser 201 below the outlet header 207 is maintained a volume of liquid nitrogen 209. Immersed in the volume 209 of liquid nitrogen is a heat exchange coil 211. The inlet end of the heat exchange coil 211 is connected to a pipeline 213 which communicates with the downstream end of the expansion valve 112. The outlet end of the heat exchange coil 211 communicates with a conduit 215 which passes through the heat exchanger 110 and may end in the inlet of another plant in which the nitrogen is to be used. Downstream of the heat exchanger 110 the conduit 215 has a pneumatically or electrically operated flow control valve 217 which is controlled by a temperature sensor 219 located downstream thereof such that gas will not flow through the valve 217 if the nitrogen has not been warmed up to a chosen temperature by the heat exchanger 110. Downstream of the valve 217 is a back pressure valve 221.

To permit discharge of uncondensed gas, the condenser 201 has an outlet 223 for uncondensed gas which communicates directly with the pipeline 142.

In operation, warm nitrogen gas passes through the heat exchange coil 211 to evaporate liquid nitrogen from the volume 209 thereof. The so-formed cold nitrogen vapour then enters the heat exchange tubes 205 through their lower ends and ascends these tubes 205 thereby cooling the mixture of nitrogen and vinyl chloride passing outside the tubes 205 to a temperature at which the vinyl chloride condenses. The evaporated nitrogen after passing through the tubes 205 leaves the condenser 201 through an outlet header 225 which communicates with the pipeline 148.

A temperature sensor 227 is located in contact with the condensed liquid leaving the region 207. Signals from the sensor 227 are used to control the setting of a solenoid operated flow-control valve 227' located in the pipeline 213. Thus, the valve 229 may be set to allow a flow of warm nitrogen gas through the heat exchange coil 211 sufficient to maintain the temperature sensed by the sensor 227 at a chosen value.

Instead of supplying the pipeline 213 with expanded nitrogen from the expansion valve 112 the plant shown in FIG. 2 also has an alternative circuit for recycling to the pipeline 213 the nitrogen evaporated from the volume 209. Thus, a conduit 231 extends from a region of the conduit 148 upstream of the valve 150 but downstream of the heat exchanger 110 and ends in the conduit 213 downstream of a shut off valve 233 disposed in the conduit 213. The conduit 231 has disposed therein a shut-off valve 235 and a pressure regulator 234 upstream of the union of the conduit 231 with the conduit 213. Using this alternative means of supplying the coil 211 with warm expanded gaseous nitrogen reduces the consumption of liquid nitrogen. If this alternative means is to be used the pressure that the gaseous nitrogen from line 215 is required at should be less than the pressure of the gas leaving the header 225, but higher than the pressure required downstream of the valve 221.

Figure 3:
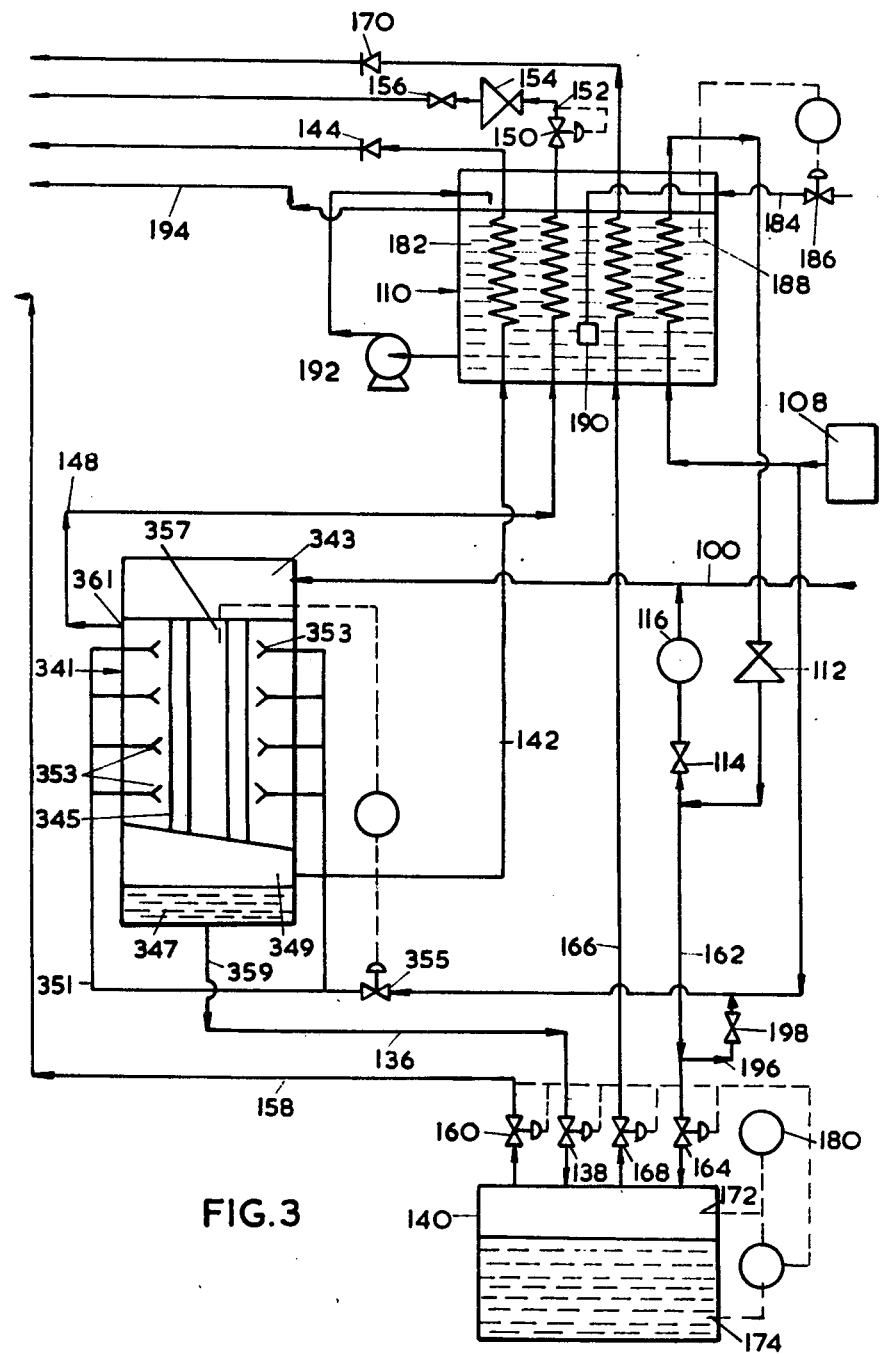
FIG. 3 is a flow diagram illustrating a third plant for performing the process according to the present invention.

Referring now to the plant shown in FIG. 3, parts of the plant identical to that shown in FIG. 1 are given the same reference numerals and are not described again. The main difference between the plant shown in FIG. 3 and that shown in FIG. 1 is that a different condenser is used.

A condenser 341 has an inlet header for process gas, which is typically a mixture of vinyl chloride and nitrogen, in communication with the pipeline 100. The inlet header 343 receives the upper ends of several heat exchange tubes 345. The lower ends of the tubes 345 terminate in a reservoir 347 for condensed vapour. Uncondensed gas disengages from the vapour and leaves the tubes through an outlet header 349. A pipeline 351 communicates at one end with the vacuum insulated evaporator 108 and at its other end with four vertically spaced apart sets of circumferentiall disposed spray headers 353. The pipeline 351 supplies liquid nitrogen to the spray headers 353 which spray liquid nitrogen onto the outer surfaces of the tubes 345. Located in the pipeline 351 is a pneumatically or electrically operated flow-control valve 355. This valve is actuated by means of a temperature sensor 357 situated in the uncondensed gas leaving the heat exchange tubes 345. The valve 355 may be programmed such that it is open only when the temperature is above a chosen value.

The reservoir has an outlet 359 which is connected directly to the conduit 136.

The outlet header 349 is connected directly to the pipeline 142.

The condenser 341 has an outlet 361 which is connected directly to the pipeline 148.

Figure 4:
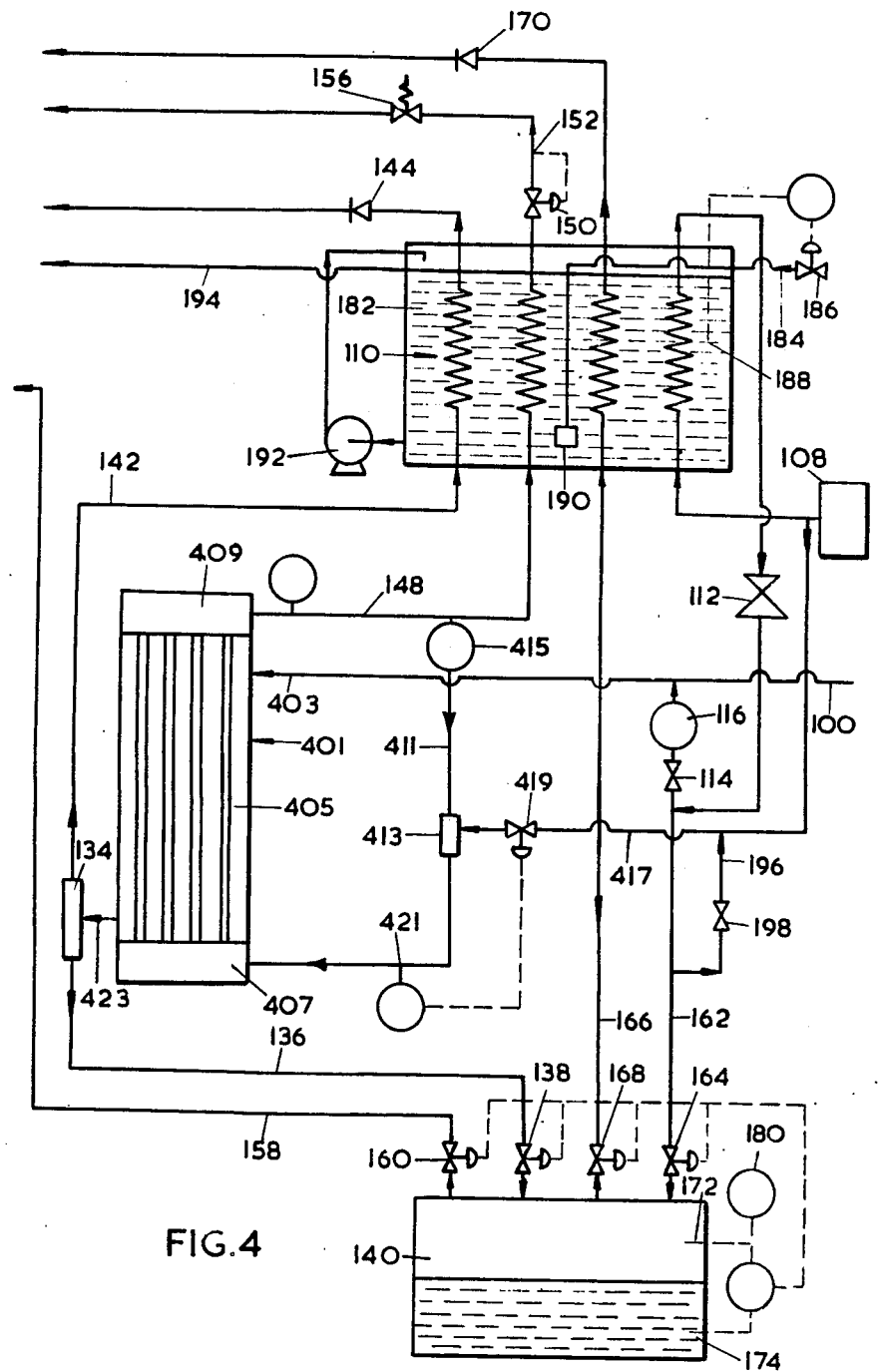
FIG. 4 is a flow diagram of a fourth plant for performing the process according to the present invention.

Referring now to FIG. 4 of the drawings, parts of the illustrated plant identical to that shown in FIG. 1 are given the same reference numerals as in FIG. 1 and are not described again. As in the plant illustrated in FIG. 2 the condenser 401 is a shell and tube heat exchanger. The condenser has an inlet 403 for process gas communicating with the space defined between the shell of the heat exchanger and several spaced apart, vertically disposed heat exchange tubes 405. Cold nitrogen gas enters the condenser 401 through an inlet header 407 which communicates with the lower ends of the heat exchange tubes 405. The cold nitrogen ascends the tubes 405 and cools the process gas outside the tubes to a temperature at which the vinyl chloride it contains condenses. Baffles (not shown) may be fitted across the condenser 401 to obtain good circulation of the process gas as it passes through the condenser 401 and thereby improve the heat exchange between the nitrogen and the process gas.

The nitrogen vapour passes out of the tubes 405 through their upper ends into an outlet header 409 which communicates with the inlet of the conduit 148.

An inlet of a nitrogen recycle line 411 extends from a region of the conduit 148 upstream of the heat exchanger 110. Its outlet ends in the inlet header of the condenser 401. Located in the recycle line 411 is a blower 415. By operation of the blower a proportion of the gas leaving the condenser 401 through the outlet header 409 is returned to the inlet header 407.

In order to produce the temperature of the recirculating nitrogen liquid nitrogen is introduced from the VIE 108 via conduit 417 into a mixer and knockout chamber 413 located in the recycle line 411 downstream of the blower 415. In the conduit 417 is situated an electrically or pneumatically operated valve 419. A temperature sensor 421 is located in thermal contact with the gas in the recycle line 411 at a region downstream of the blower 415. In operation, the sensor 421 generates signals which actuate the control circuits of the valve 419 so as to operate this valve such that the sensed temperature is kept at or close to a chosen temperature which corresponds to the temperature at which it is desired that the condensed vinyl chloride should be obtained.

The condensed vinyl chloride and uncondensed gas leaves the condenser 401 through an outlet 423 which communicates with the phase separator 134.

It may frequently be preferred to arrange the connections to the shell and tube heat exchanger shown in FIG. 4 such that the gas mixture containing vinyl chloride is passed through the tubes and the refrigerant nitrogen outside the tubes.

Figure 5:
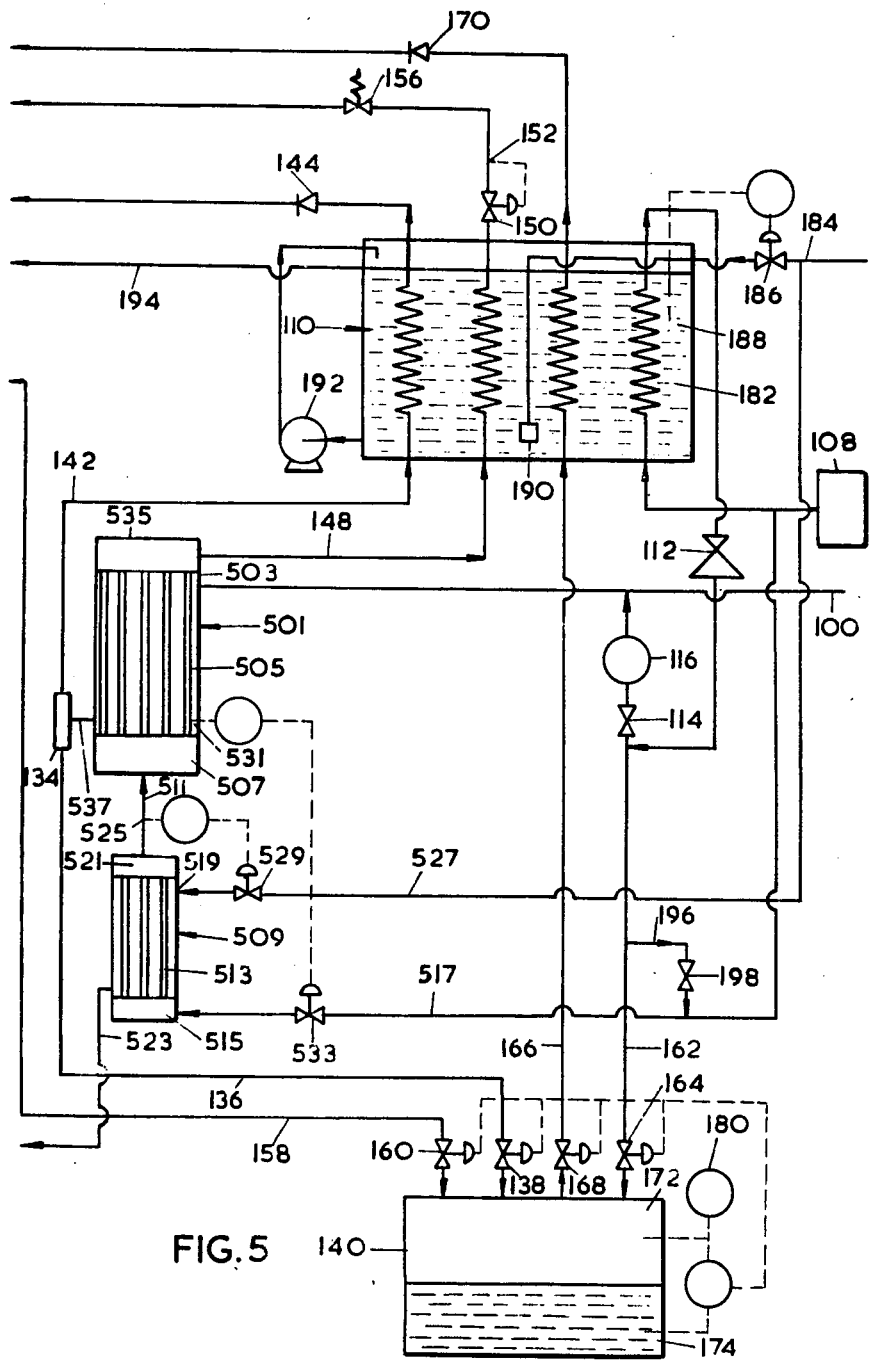
FIG. 5 is a flow diagram of a fifth plant for performing the process according to the present invention.

Referring now to FIG. 5 of the drawings, parts of the illustrated plant identical to that shown in FIG. 1 of the drawings are given the same reference numerals as in FIG. 1 and are not described again.

A condenser 501, again a shell and tube heat exchanger, has an inlet 503 for process gas. The inlet 503 communicates with the space defined between the shell of the condenser and several spaced apart, vertically disposed heat exchange tubes 505. Cold nitrogen gas enters the condenser 501 through an inlet header 507 which receives the lower ends of the heat exchanger tubes 505. The nitrogen is supplied to the inlet header 507 through a pipe 511 connecting the condenser 501 to another shell and the tube heat exchanger 509. Liquid nitrogen is passed into an inlet header 515 (in which the lower ends of the heat exchange tubes 513 of the heat exchanger 509 are received) from vacuum insulated evaporator 108 via conduit 517. The liquid nitrogen ascends the tubes and is evaporated by heat exchange with steam admitted to an inlet 519 in communication with the space defined between the shell and the tubes 515 of the heat exchanger 509. The inlet 519 is connected to the outlet of a conduit 527 whose inlet communicates with the conduit 184 upstream of the valve 186. Thus steam is able to be passed into the heat exchanger.

The temperature of the nitrogen entering the condenser 501 is controlled by means of a temperature sensor 525 located in the pipe 511. The temperature sensor 525 generates signals which actuate the control circuits of an electrically or pneumatically operated flow control valve 529 in the conduit 527 so as to operate the valve 529 such that the sensed temperature is kept at or close to a chosen value.

The flow of nitrogen through the condenser 501 may be controlled by means of a temperature sensor 531 located in the condenser 501 at a region where there collects vinyl chloride condensed from the process gas, admitted through the inlet 503, by heat exchange with the nitrogen entering the condenser 501 through the inlet header 507. The sensor 531 may be arranged to generate signals which actuate the control circuits of an electrically or pneumatically operated flow control valve 533 located in the conduit 517 so as to operate the valve such that the sensed temperature of the condensed vinyl chloride is kept at or close to a chosen value. Thus, if the sensed temperature falls below the chosen value the flow rate of liquid nitrogen is reduced by operation of the valve 533, if the sensed temperature rises above the chosen value the value 531 is operated to increase the flow rate of liquid nitrogen into the heat exchanger 509.

Nitrogen leaving the tubes 505 of the condenser 501 passes into an outlet header 535 which communicates with the conduit 148. Condensed vinyl chloride and uncondensed gas leaves the condenser 501 through outlet 537 which communicates with the phase separator 134.

It may frequently be preferred to arrange the connections to the shell-and-tube heat exchanger shown in FIG. 5 of such that the gas containing vinyl chloride passes through the tubes and the refrigerant nitrogen passes outside the tubes.

Figure 6:
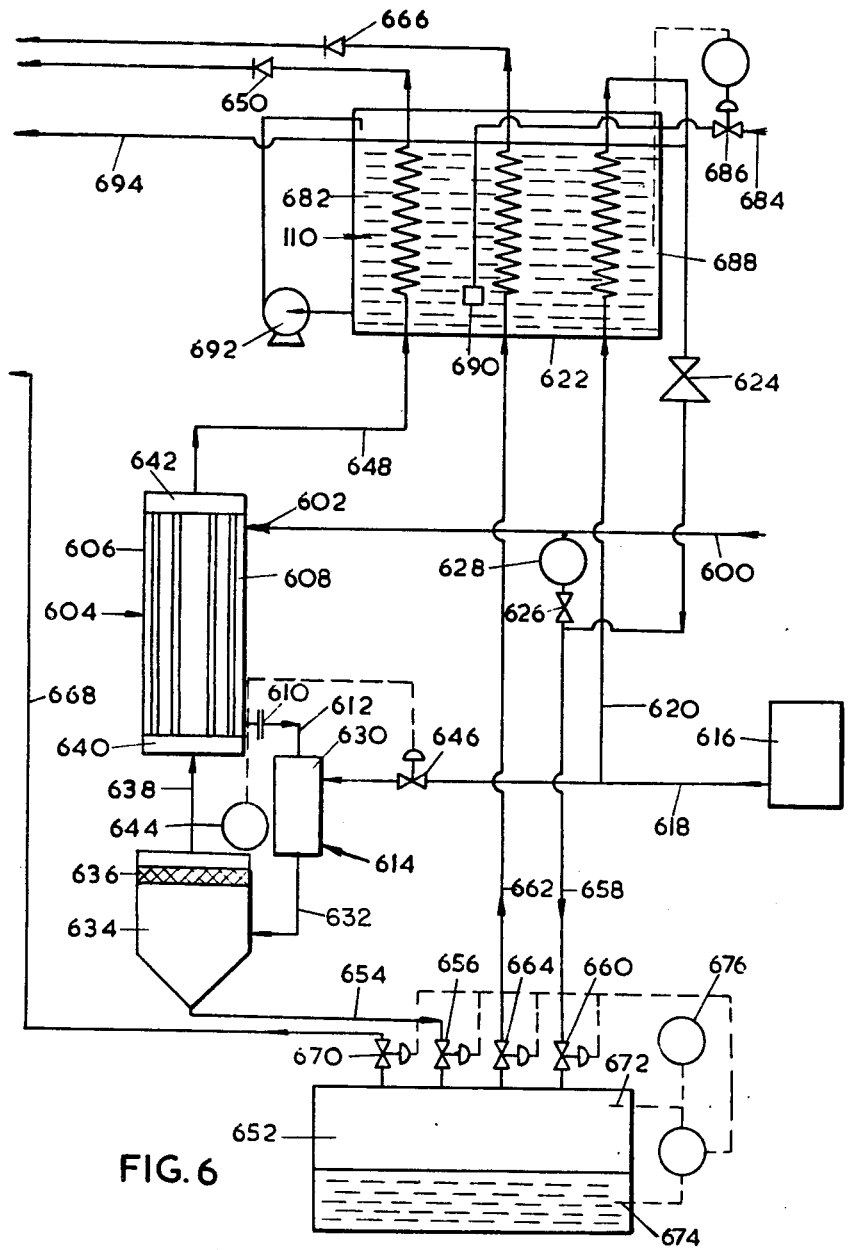
FIG. 6 is a flow diagram of a sixth plant for performing the process according to the present invention.

Referring now to FIG. 6 of the drawings a plant in which the refrigerant is contacted directly with the process gas is shown. Process gas which may for example include or consist of vinyl chloride mixed if desired with nitrogen enters the plant through pipeline 600. Liquid nitrogen from a vacuum insulated evaporator 616 is passed through line 618 into conduit 620 which passes through a heat exchanger 622 in which the liquid nitrogen is evaporated and warmed to approximately ambient temperature. From the heat exchanger 622 the warm nitrogen passes through an expansion valve 624 and a manual control valve 626 whereby its pressure is reduced to that of the process gas entering the pipeline 600. The expanded nitrogen is metered through a flow indicator 628 which is controlled by the valve 626 upstream thereof and which is adapted to introduce nitrogen into the pipeline 600 at a predetermined rate.

The mixture of nitrogen and vinyl chloride passes from the pipeline 600 into an inlet 602 of a shell-and-tube heat exchanger 604. The shell and tube heat exchanger has a shell or container 606 in which are disposed several spaced-apart vertically disposed heat exchanger tubes 608. The inlet 602 communicates with the space defined between the shell 606 and the tubes 608. The process gas passes downwardly through this space as is pre-cooled by heat exchanger with cold fluid passing through the tubes 608. The pre-cooled gas leaves the heat exchanger 604 through an outlet 610 which communicates with the inlet of a pipe 612 whose outlet terminates in a condenser 614. The pre-cooled gas thus enters the condenser 614.

Liquid nitorgen from the vacuum-insulated evaporator 616 is sprayed into the condenser 614 through spray-headers 630. The liquid nitrogen is passed from the evaporator 616 into the spray headers 630 via the line 618. The liquid nitrogen sprayed into the condenser 616 condenses vinyl chloride from the process gas and is itself evaporated. The resulting mixture of condensed vinyl chloride and nitrogen gas leaves the condenser 614 through an outlet 632 which communicates with the inlet of a phase separator 634 with a demister section 636. In this separator the condensed vinyl chloride is separated from the gaseous nitrogen.

The gaseous nitrogen leaves the separator 634 through an outlet line 638 which communicates with an inlet header 640 of the heat exchanger 604. It is this nitrogen which acts as the cooling fluid to pre-cool the incoming nitrogen. It enters the heat exchanger tubes 608, ascends the heat exchanger 604 through them and passes out of them into an outlet header 642.

In order to control the temperature at which the condensate is collected in the separator 634, a temperature sensor 644 is located in the line 638. It generates signals which actuate the control circuits of a pneumatically or electrically operated flow control valve 646 located in the line 618 downstream of the union of the latter with the conduit 620.

The valve 646 is programmed such that if the sensed temperature falls below a chosen value its setting adjusts automatically so as to reduce the rate at which liquid nitrogen is sprayed into the condenser 614, and if the sensed temperature rises above a chosen value its setting adjusts automatically so as to increase the rate at which liquid nitrogen is sprayed into the condenser. By this means the temperature of the gas leaving the separator 634 may be kept at or close to a chosen value.

From the outlet header 642 of the heat exchanger 604 the gas passes into a conduit 648 which extends through the heat exchanger 622 and has disposed therein, at a region downstream of the heat exchanger 622, a non-return valve 650. After passing through the non-return valve the gas may be vented.

The liquid from the separator 634 is passed into a storage tank 652 via a conduit 654 having an electrically or pneumatically operated valve 656 disposed therein. The tank 652 also has a valved inlet pipe 658 for gaseous nitrogen. Pipe 658 communicates with the downstream end of the expansion valve 624 and thus receives evaporated nitrogen from the evaparator 616 via the heat exchanger 622. Alternatively, a line (not shown) may be taken directly from the ullage space of the heat exchanger 608 via a pressure control valve (not shown) to provide cold gas for this purpose. In the pipe 658 is situated a pneumatically or electrically operated valve 660. The tank 652 also has an outlet line 662 which extends through the heat exchanger 622 and from which gas from the ullage space of the tank 652 may be vented. The outlet line 662 has near its inlet a pneumatically or electrically operated valve 664. In addition, downstream of the heat exchanger 622 is a non-return valve 666 disposed in the line 662. The tank 652 also has an outlet line 668 through which condensed vinyl chloride can be transferred from the tank 652. The line 668 has near its inlet a pneumatically or electrically operated valve 670 disposed therein.

In normal operation of the tank 652 the valves 656 and 644 will remain open to permit condensed vinyl chloride to flow into the tank 622 from the phase separator 634. The valves 670 and 660 will generally be closed. When the level of vinyl chloride in the tank 622 reaches that of an upper level detector 672 located therein the valves may be actuated in the following time controlled sequence. First the valves 656 and 664 are closed to prevent further entry of condensed vinyl chloride into the tank 652 or venting of vapour therefrom. Second, the valve 670 is opened. Third, the valve 660 is opened so as to permit nitrogen to pass into the ullage space of the tank 652 and to create in the ullage space a pressure sufficient to transfer liquid from the tank 652. During the transfer period, vinyl chloride may still be condensed. The separator 634 should desirably have a sufficiently large volume to be able to collect condensate during the transfer period without the operation of the condenser 614 being impaired. When the level of the liquid in the tank 652 has fallen to that of a lower level detector 674 the valves 660 and 670 are closed. A chosen time afterwards the valve 664 is opened to permit the ullage space of the tank 652 to be vented. A chosen time afterwards the valve 656 is reopened so as to enable introduction of the condensed vinyl chloride into the tank 652 to take place again. If desired, the tank 652 may be fitted with an automatic alarm 676 such that if the level of condensed vinyl chloride therein remains at or above that of the detector 672 for a chosen time the alarm 676 will sound.

The streams passing through the heat exchanger 622 are warmed by a volume of hot water 682 maintained therein. The water 682 is heated by steam, typically at 80 psig, admitted into the heat exchanger 622 through a pipeline 684. The pipeline 684 has disposed therein a mechanically operated flow control valve 686. The setting of the valve 686 may be adjusted automatically by means of signals generated by a temperature sensor 688 located in the volume of water at a chosen temperature, say 80° C. The pipeline 684 ends in a silencer 690 through which the steam is introduced into the volume of water 682. To ensure that the water is kept at an approximately uniform temperature at all levels in the heat exchanger 622 a pump 692 may be provided so as to transfer water from the bottom of the heat exchanger 622 to a region near the top thereof. In addition, the heat exchanger 622 is provided with an outlet 694 through which excess water is discharged.

Depending on the constituents of the incoming process gas it may be possible to use treated process gas vented from lines 648 and 662 as, for example, an inerting gas in chemical process operated on the same site as that where the plant illustrated in FIG. 6 is situated. This will be frequently possible if the incoming gas consist of nitrogen and condensible vapour such as vinyl chloride with only minor proportions of unwanted impurities. The vented gas may be used for duties such as 'inerting' storage tanks or chemical reactors, especially if the tanks or reacts receive in their normal operation vinyl chloride or other condensible compound or some other substance compatible with or insensitive to any vapour contained in the gas vented from the lines 648 and 662.

If the vinyl chloride is likely to condense in the heat exchanger 604 during operation of the plant shown in FIG. 6, the plant may be provided with an additional phase separator (not shown). This additional phase separator will be located in communication with the pipe 612 and will supply liquid to the separator 634 and allow the uncondensed gas to pass into the condenser 614.

In the plant shown in FIG. 6, it may alternatively be arranged for the incoming gas containing vinyl chloride to be passed through the tubes of the tube and shell heat exchanger and for the uncondensed gas from the separator 634 to be passed outside the tubes.

We claim:

1. A process for condensing the vapour of a volatile liquid comprising the steps of: taking a stream of gaseous mixture comprising the vapour of the volatile liquid and a non-flammable gas; condensing at a controlled temperature the vapour from said stream while leaving the non-flammable gas uncondensed by cooling the stream of gas mixture with refrigerant, the controlled temperature being between the boiling point of the volatile liquid at atmospheric pressure and the boiling point of the refrigerant at atmospheric pressure and also between the boiling and freezing points of the volatile liquid at the prevailing pressure at which the condensate is formed; forming the refrigerant by taking liquid nitrogen from a souce thereof; and collecting the condensate; warming the uncondensed gas to a temperature at or near to ambient temperature; and venting the uncondensed gas and vaporized nitrogen.

2. A process as claimed in claim 1, in which the vapour of the volatile liquid is condensed in a condenser including a container through which at least one conduit conducts the gaseous mixture, the conduit being at least partially immersed in a volume of liquid refrigerant held in the container, whereby the temperature of the gaseous mixture is reduced to the controlled temperature at which the cryogenic liquid boils, which temperature is predetermined by subjecting the liquid refrigerant to a selected pressure.

3. A process as claimed in claim 1, in which the indirect heat exchange is effected by passing the gaseous mixture through at least one heat exchange, sensing the temperature of the liquid condensate and uncondensed gas, and spraying the conduit with liquid refrigerant when the sensed temperature is above controlled temperature.

4. A process as claimed in claim 1, in which the heat exchange is effected in a condenser including a container holding a volume of liquid refrigerant, the liquid refrigerant being evaporated by being heated, and the so-formed refrigerant vapour being contacted in the container with the outer surface of at least one heat exchange conduit through which the gaseous mixture is passed.

5. A process as claimed in claim 1, in which the liquid refrigerant is evaporated outside the condenser in which the evaporated liquid refrigerant is indirectly heat exchanged with the gaseous medium.

6. A process as claimed in claim 5, in which the portion of the evaporated liquid refrigerant after it is has passed out of the condenser is returned thereto.

7. A process as claimed in claim 6, in which liquid refrigerant is introduced into the vapour being returned to the condenser, the liquid refrigerant so introduced vaporising before it enters the condenser.

8. A process as claimed in claim 7 in which the temperature of the evaporated liquid refrigerant entering the condenser is sensed and the temperature of the evaporated liquid refrigerant entering the condenser is kept at or close to the controlled temperature by appropriately controlling the introduction of the liquid refrigerant into the vapour being returned to the condenser.

9. A process as claimed in claim 5, in which the liquid refrigerant is evaporated by heat exchange with a fluid which is kept separate from the refrigerant, and which is not heat exchanged with the gaseous mixture to be condensed.

10. A process as claimed in claim 9, in which the condensate is formed at approximately the controlled temperature by introducing the evaporated liquid refrigerant into the condenser at the controlled temperature and at a controlled rate.

11. A process as claimed in claim 10, in which temperature of the evaporated liquid refrigerant after heat exchange with the heat exchange fluid is sensed, and the flow rate of the refrigerant undergoing heat exchange with the heat exchange liquid is controlled so as to keep the sensed temperature at approximately the controlled temperature.

12. A process as claimed in claim 11 in which the temperature of the condensate or of the uncondensed gas is sensed, and the rate at which evaporated liquid refrigerant is introduced into the condenser is controlled so as to keep the sensed temperature at approximately the controlled temperature.

13. A process as claimed in claim 1, in which the gaseous mixture is pre-cooled by heat exchange with the said uncondensed gas, vapour of the volatile liquid condensed during the pre-cooling is separated from the uncondensed gas before the main condensation is performed, and liquid refrigerant is contacted directly with the pre-cooled uncondensed gas.

14. A process as claimed in claim 13, in which the temperature at which the condensate is collected is controlled by sensing the temperature, the uncondensed gas before it is heat exchanged with incoming gaseous mixture, and then employing signals generated by sensing the temperature to control the setting of a flow-control valve in a conduit through which the liquid refrigerant is supplied to the condenser so as to keep the sensed temperature at approximately the controlled temperature.

15. A process as claimed in claim 1, in which the gaseous mixture contains impurities, which freeze at the temperature and pressure at which the vapour is condensed, which impurities are separated from the gaseous mixture before the condensation.

16. A process as claimed in claim 1, in which there is a single refrigerant.

17. A process as claimed in claim 1, in which the volatile liquid is of the vinyl chloride monomer, ethylene dichloride, acrylonitrile and vinyl acetate.

18. A process as claimed in claim 1, in which the liquid nitrogen is vaporized on coming into heat exchange relationship with the gaseous mixture.

19. A process as claimed in claim 1, in which the liquid nitrogen is vaporized upstream of where it comes into heat exchange relationship with the gaseous mixture.

* * * * *